US011504068B2

(12) United States Patent
Patel et al.

(10) Patent No.: US 11,504,068 B2
(45) Date of Patent: *Nov. 22, 2022

(54) METHODS, SYSTEMS, AND MEDIA FOR PREDICTING SENSOR MEASUREMENT QUALITY

(71) Applicant: Google LLC, Mountain View, CA (US)

(72) Inventors: Yojan Patel, London (GB); Melissa Frank, Los Altos, CA (US)

(73) Assignee: Google LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/201,400

(22) Filed: Mar. 15, 2021

(65) Prior Publication Data

US 2021/0196204 A1   Jul. 1, 2021

Related U.S. Application Data

(63) Continuation of application No. 15/840,467, filed on Dec. 13, 2017, now Pat. No. 10,945,674.

(51) Int. Cl.
*A61B 5/00* (2006.01)
*A61B 5/024* (2006.01)
*G16H 20/30* (2018.01)

(52) U.S. Cl.
CPC ............ *A61B 5/721* (2013.01); *A61B 5/0002* (2013.01); *A61B 5/02405* (2013.01);
(Continued)

(58) Field of Classification Search
CPC .................................................... A61B 5/721
(Continued)

(56) References Cited

U.S. PATENT DOCUMENTS 6,842,877 B2 * 1/2005 Robarts ................. G06F 21/606
715/708
8,945,017 B2   2/2015 Venkatraman et al.
(Continued)

FOREIGN PATENT DOCUMENTS

WO   WO 2017079580   5/2017

OTHER PUBLICATIONS

International Search Report and Written Opinion dated Jan. 7, 2019 in International Patent Application No. PCT/US2018/051051.
(Continued)

*Primary Examiner* — Ricky Go
(74) *Attorney, Agent, or Firm* — Byrne Poh LLP (57) ABSTRACT

Methods, systems, and method for predicting sensor measurement quality. In some implementations, the method comprises: measuring, using a wearable computing device that includes a processor and a sensor, information indicating motion of the wearable computing device during a current time period; identifying one or more parameters associated with a determination of a likelihood that one or more measurements from the sensor configured within the wearable computing device is of sufficient quality for calculating a physiological metric using the one or more measurements from the sensor, wherein the one or more parameters include contextual parameters associated with the wearable computing device; determining the likelihood that the measurement from the sensor associated with the user device is of sufficient quality at a second time period for calculating the physiological metric using the measurement from the sensor based on the identified one or more parameters and based on the information indicating the motion of the user device during the current time period; in response to determining that the likelihood exceeds a predetermined threshold, activating the processor and the sensor and col-
(Continued)

lecting a measurement from the sensor at the second time period; and updating the identified one or more parameters based on the motion of the user device during the current time period and based on the measurement from the sensor at the second time period.

20 Claims, 4 Drawing Sheets

(52) U.S. Cl.
CPC ...... *A61B 5/02416* (2013.01); *A61B 5/02438* (2013.01); *A61B 5/7267* (2013.01); *G16H 20/30* (2018.01); *A61B 2562/0219* (2013.01)

(58) Field of Classification Search
USPC ........................................................ 702/127
See application file for complete search history.

(56) References Cited

U.S. PATENT DOCUMENTS

| | | | |
|---|---|---|---|
| 9,662,023 B2 | 5/2017 | Samandi et al. | |
| 9,675,281 B2 | 6/2017 | Arnold et al. | |
| 9,729,693 B1 | 8/2017 | Munaretto | |
| 9,743,848 B2 | 8/2017 | Breslow et al. | |
| 9,854,292 B1* | 12/2017 | Matthews | H04N 21/6582 |
| 2012/0123232 A1* | 5/2012 | Najarian | A61B 5/7203 |
| | | | 600/345 |
| 2014/0073486 A1 | 3/2014 | Ahmed et al. | |
| 2014/0275854 A1 | 9/2014 | Venkatraman et al. | |
| 2016/0007934 A1 | 1/2016 | Arnold et al. | |
| 2016/0058367 A1 | 3/2016 | Raghuram et al. | |
| 2016/0249174 A1 | 8/2016 | Patel et al. | |
| 2017/0196497 A1 | 7/2017 | Ray et al. | |
| 2018/0056123 A1* | 3/2018 | Narasimha Rao | A63B 24/0062 |
| 2019/0110755 A1 | 4/2019 | Capodilupo et al. | |

OTHER PUBLICATIONS

Notice of Allowance dated Nov. 6, 2020 in U.S. Appl. No. 15/840,467.
Office Action dated Jan. 10, 2020 in U.S. Appl. No. 15/840,467.
Office Action dated Jul. 10, 2020 in U.S. Appl. No. 15/840,467.
Examination Report dated Jun. 30, 2021 in IN Patent Application No. 201947048316.

* cited by examiner

METHODS, SYSTEMS, AND MEDIA FOR PREDICTING SENSOR MEASUREMENT QUALITY

CROSS-REFERENCE TO RELATED APPLICATION

This application is a continuation of U.S. patent application Ser. No. 15/840,467, filed Dec. 13, 2017, which is hereby incorporated by reference herein in its entirety.

TECHNICAL FIELD

The disclosed subject matter relates to methods, systems, and media for predicting sensor measurement quality. More particularly, the disclosed subject matter relates to analyzing, at a current time period, sensor information and/or contextual information associated with a wearable computing device to determine whether to obtain additional sensor information or perform analysis of such sensor information at a subsequent time period.

BACKGROUND

People are increasingly interested in using wearable computing devices, such as fitness trackers or smartwatches, to measure different physiological parameters, such as heart rate or heart rate variability. Measuring or determining a physiological parameter is often done based on sensor readings, for example, using a photoplethysmographic sensor to generate photoplethysmographic data (e.g., a photoplethysmographic waveform) that can be used to calculate a physiological parameter, such as heart rate or heart rate variability.

The performance of such a sensor used for determining a physiological parameter, however, is typically dependent on factors such as motion. For example, a sensor reading from a photoplethysmographic sensor may lack accuracy if the user is in motion. Nevertheless, many devices that include these sensors typically make measurements at fixed intervals, regardless of whether the measurements are likely to be noisy or useful for calculating a physiological parameter, such as heart rate variability. This can be resource intensive, for example, causing the device to unnecessarily consume power by waking up a processor that, in turn, activates one or more sensors to make sensor measurements that are not of sufficient quality to be used in calculating the desired physiological parameter. Moreover, these collected sensor measurements that are not of sufficient quality are often discarded.

Accordingly, it is desirable to provide new methods, systems, and media for predicting sensor measurement quality.

SUMMARY

Methods, systems, and media for predicting sensor measurement quality are provided.

In accordance with some implementations of the disclosed subject matter, a method for predicting sensor measurement quality is provided, the method comprising: measuring, using a wearable computing device that includes a processor and a sensor, information indicating motion of the wearable computing device during a current time period; identifying one or more parameters associated with a determination of a likelihood that one or more measurements from the sensor configured within the wearable computing device is of sufficient quality for calculating a physiological metric using the one or more measurements from the sensor; determining the likelihood that the measurement from the sensor associated with the user device is of sufficient quality at a second time period for calculating the physiological metric using the measurement from the sensor based on the identified one or more parameters and based on the information indicating the motion of the user device during the current time period; in response to determining that the likelihood exceeds a predetermined threshold, activating the processor and the sensor and collecting a measurement from the sensor at the second time period; and updating the identified one or more parameters based on the motion of the user device during the current time period and based on the measurement from the sensor at the second time period.

In some implementations, the sensor is a photoplethysmography sensor and the physiological metric is heart rate variability of a user of the wearable computing device.

In some implementations, the method further comprises determining contextual information associated with the wearable computing device, wherein the likelihood that the measurement from the sensor is of sufficient quality at the second time period for calculating the physiological metric using the measurement from the sensor is based on the identified one or more parameters, the information indicating the motion of the user device during the current time period, and the determined contextual information associated with the wearable computing device.

In some implementations, the one or more parameters include a threshold associated with the information indicating the motion of the user device during the current time period, and the likelihood is determined based on the threshold associated with information indicating the motion of the user device.

In some implementations, the information indicating the motion of the user device includes an acceleration of the user device, and wherein the threshold associated with the information indicating the motion of the user device is a mean acceleration measured during the current time period.

In some implementations, the parameters are determined based on a training set comprising a plurality of training samples, wherein a training sample from the plurality of training samples includes the information indicating the motion of the user device and a corresponding sensor measurement.

In some implementations, the method further comprises, in response to determining that the likelihood does not exceed the predetermined threshold, causing the identified one or more parameters to be updated and inhibiting the processor and the sensor of the wearable computing device from being activated.

In accordance with some implementations of the disclosed subject matter, a system for predicting sensor measurement quality is provided, the system comprising a sensor and a hardware processor connected to the sensor, wherein the hardware processor is configured to: measure information indicating motion of the wearable computing device during a current time period; identify one or more parameters associated with a determination of a likelihood that one or more measurements from the sensor configured within the wearable computing device is of sufficient quality for calculating a physiological metric using the one or more measurements from the sensor; determine the likelihood that the measurement from the sensor associated with the user device is of sufficient quality at a second time period for calculating the physiological metric using the measurement from the sensor based on the identified one or more parameters and based on the information indicating the motion of the user device during the current time period; in response to determining that the likelihood exceeds a predetermined threshold, activate the processor and the sensor and collect a measurement from the sensor at the second time period; and update the identified one or more parameters based on the motion of the user device during the current time period and based on the measurement from the sensor at the second time period.

In accordance with some implementations of the disclosed subject matter, a non-transitory computer-readable medium containing computer executable instructions that, when executed by a processor, cause the processor to perform a method for predicting sensor measurement quality is provided, the method comprising: measuring, using a wearable computing device that includes a processor and a sensor, information indicating motion of the wearable computing device during a current time period; identifying one or more parameters associated with a determination of a likelihood that one or more measurements from the sensor configured within the wearable computing device is of sufficient quality for calculating a physiological metric using the one or more measurements from the sensor; determining the likelihood that the measurement from the sensor associated with the user device is of sufficient quality at a second time period for calculating the physiological metric using the measurement from the sensor based on the identified one or more parameters and based on the information indicating the motion of the user device during the current time period; in response to determining that the likelihood exceeds a predetermined threshold, activating the processor and the sensor and collecting a measurement from the sensor at the second time period; and updating the identified one or more parameters based on the motion of the user device during the current time period and based on the measurement from the sensor at the second time period.

In accordance with some implementations of the disclosed subject matter, a system for predicting sensor measurement quality is provided, the system comprising: means for measuring information indicating motion of the wearable computing device during a current time period; means for identifying one or more parameters associated with a determination of a likelihood that one or more measurements from a sensor configured within the wearable computing device is of sufficient quality for calculating a physiological metric using the one or more measurements from the sensor; means for determining the likelihood that the measurement from the sensor associated with the user device is of sufficient quality at a second time period for calculating the physiological metric using the measurement from the sensor based on the identified one or more parameters and based on the information indicating the motion of the user device during the current time period; in response to determining that the likelihood exceeds a predetermined threshold, means for activating the processor and the sensor and means for collecting a measurement from the sensor at the second time period; and means for updating the identified one or more parameters based on the motion of the user device during the current time period and based on the measurement from the sensor at the second time period.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

In accordance with various implementations, mechanisms (which can include methods, systems, and media) for predicting sensor measurement quality are provided.

In some implementations, the mechanisms described herein can determine a likelihood that a sensor associated with a user device (e.g., a wearable computing device, such as a fitness tracker or smartwatch, etc.) will make a measurement of relatively high quality and/or that is of sufficient quality such that it can be used to calculate a particular metric, such as a physiological parameter of a user of the user device. For example, in some implementations, the sensor can be a photoplethysmograph (PPG) sensor configured on a wearable computing device in which the sensor can be used to measure or infer a heartbeat of a user of the wearable computing device. In some such implementations, the mechanisms can calculate a likelihood that a reading from the PPG sensor will be of high enough quality to infer the heartbeat of the user, that the reading will be of high enough quality to calculate a heart rate or heart rate variability (HRV) of the user, and/or calculate any other suitable metrics.

In some implementations, the mechanisms can calculate the likelihood that the sensor reading will be of sufficiently high quality based on any suitable information. For example, in some implementations, the likelihood can be calculated based on motion data associated with the user device that indicates acceleration of the user device over a particular time window (e.g., ten seconds, and/or any other suitable duration of time). As another example, in some implementations, the likelihood can be calculated based on contextual information associated with the user device, such as a time of day, ambient environmental conditions (e.g., an amount of ambient light, an ambient temperature, and/or any other suitable environmental conditions), a current user activity, and/or any other suitable contextual information.

In some implementations, the mechanisms described herein can train any suitable algorithm that can be used to calculate the likelihood. For example, in some implementations, the mechanisms can train a thresholding algorithm, a feature-based classifier, a neural network, and/or any other suitable type of algorithm, as described below in more detail in connection with FIG. 2. In some implementations, the mechanisms can construct training samples based on motion data, contextual data, and/or previous sensor readings to train an algorithm. In some implementations, the mechanisms can update the training samples, and, therefore, update the algorithm with new training samples over time.

In some implementations, the mechanisms described herein can be used to allow a user device, such as a fitness tracker or a smartwatch, to operate more efficiently by collecting sensor data only when a calculated likelihood indicates that the sensor reading is likely to be of sufficiently high quality. By not unnecessarily collecting sensor readings and calculating metrics (e.g., heart rate, HRV, and/or any other suitable metrics) in instances where the mechanisms determine that the sensor readings or resulting metrics are likely to be inaccurate or too noisy (e.g., a noise level greater than a particular threshold value), the user device can reduce power consumption and save battery life. For example, the mechanism can determine at which instances to activate a processor and one or more sensors on a user device in response to determining that collected sensor readings would be of sufficient quality (e.g., a quality score greater than a particular quality threshold).

Figure 1:
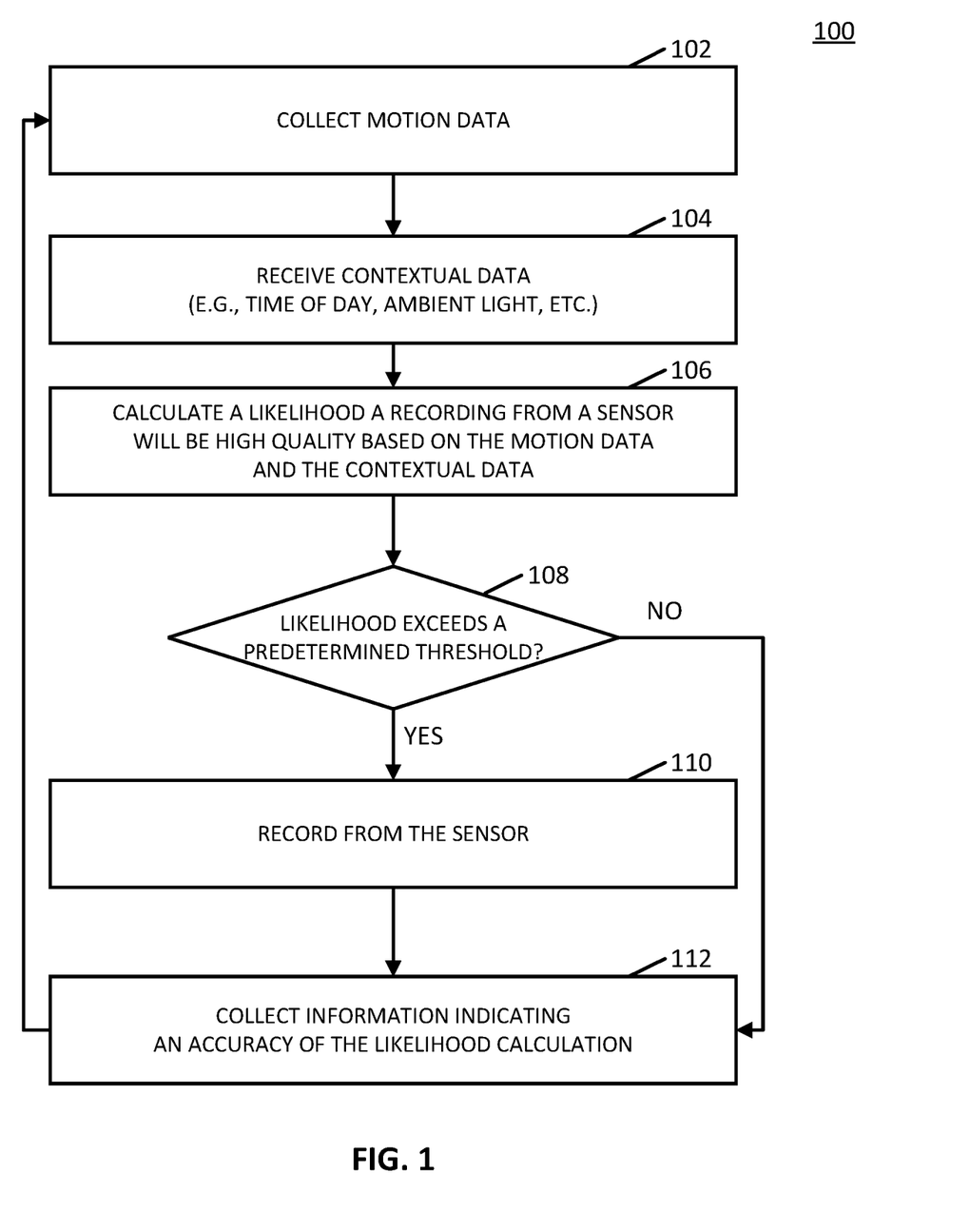
FIG. 1 shows an example of a process for determining whether to make a sensor measurement or otherwise obtain sensor information in accordance with some implementations of the disclosed subject matter.

Turning to FIG. 1, an example 100 of a process for determining whether to collect a measurement from a sensor is shown in accordance with some implementations of the disclosed subject matter. In some implementations, blocks of process 100 can be implemented on any suitable user device, such as a wearable computing device (e.g., a fitness tracker, and/or any other suitable type of user device), a mobile phone, and/or any other suitable type of user device.

Process 100 can begin by collecting data indicative of current motion of the user device at 102. In some implementations, process 100 can collect the motion data in any suitable manner. For example, in some implementations, process 100 can sample a motion sensor associated with the user device, such as an accelerometer, a gyroscope, and/or any other suitable type of motion sensor. In some implementations, process 100 can collect data representing motion of the user device that spans any suitable time range (e.g., ten milliseconds of motion data, one second of motion data, and/or any other suitable time range). In some implementations, the collected data can include any suitable number of measurement samples.

Process 100 can determine contextual information associated with the user device and/or a user of the user device at 104. In some implementations, the contextual information can include information about an environment in which the user device is currently located. For example, in some implementations, the contextual information can include a current temperature (e.g., a current ambient temperature inside a room the user device is currently located, a current outside temperature for a geographic location in which the user device is currently located, and/or a current temperature for any other suitable location). As another example, in some implementations, the contextual information can include a current time of day, a current day of the week, a current time of the year, and/or any other suitable timing information. As yet another example, in some implementations, the contextual information can include an amount of light in a room the user device is currently located in.

In some implementations, the contextual information can include information about an activity that a user of the user device is currently participating in. For example, in some implementations, the contextual information can indicate whether the user is currently watching television or otherwise consuming media content, sleeping, exercising (e.g., including a particular type of exercise), working at a computer, and/or performing any other suitable type of activity. In some implementations, contextual information indicating an activity that a user of the user device is participating in can be determined based on any suitable information. For example, in some implementations, process 100 can determine the current activity based on explicit information provided by the user, such an indication via an interface or via an input device on the user device that the user is starting a run, an indication that the user is going to sleep, and/or any other suitable type of indication. As another example, in some implementations, process 100 can infer the current activity based on any suitable information. As a more particular example, in some implementations, process 100 can determine that a user is likely to be working at a computer based on location information (e.g., based on Global Positioning System coordinates, and/or any other suitable location information) indicating that the user is at work and motion data indicating that the user is not moving around. As another more particular example, in some implementations, process 100 can determine that a user is likely running based on location information or motion data indicating that the user is currently moving at a particular pace (e.g., a particular number of miles per hour, a particular number of steps per minute, and/or any other suitable pace metric). As yet another particular example, in some implementations, process 100 can determine that a user is likely sleeping based on motion data indicating that a user is not moving or is not moving very much, ambient light information indicating that the user device is in a dark environment, and/or timing information indicating that a current time of day is between particular hours of the day (e.g., between 10 p.m. and 6 a.m., and/or any other suitable hours).

At 106, process 100 can calculate a likelihood that a recording from a sensor associated with the user device will be of relatively high quality and/or of sufficiently high quality for a particular calculation based on the motion data and/or the contextual data. For example, in some implementations, process 100 can calculate a likelihood that a sensor reading for a time period subsequent to the time period over which motion data was collected (as described above in connection with block 102) will be of relatively high quality and/or of sufficiently high quality for a particular calculation. In some implementations, the sensor can be any suitable type of sensor, such as a photoplethysmograph (PPG) sensor used for calculating a user's heart rate. In some implementations, process 100 can calculate a likelihood that a recording from the sensor will yield data of high enough quality to calculate a particular metric. For example, in instances where the sensor is a PPG sensor, process 100 can calculate a likelihood that a recording from the PPG sensor will be of high enough quality to determine heartbeats of the user, calculate a heart rate of the user, calculate an HRV of the user, calculate a respiration rate of the user, and/or any other suitable metric. As a specific example, in instances where the user device is a wearable computing device (e.g., a fitness tracker, a smartwatch, etc.) worn on a wrist or arm of a user and where the sensor is a PPG sensor, process 100 can calculate a likelihood that the wrist or the arm of the user will remain still enough for a duration of a recording from the PPG sensor such that data from the recording from the PPG sensor can be used to extract peaks corresponding to heartbeats of the user to determine heart rate and/or HRV. In continuing this example, process 100 can calculate a likelihood that a recording from the PPG sensor will be at least a given quality to determine a first type of metric (e.g., a heart rate of the user wearing the wearable computing device) but will not be at least a given quality to determine a second type of metric.

It should be noted that process 100 can determine the likelihood that a recording from the sensor will be of relatively high quality and/or useful for a particular calculation using any suitable technique or combination of techniques. For example, in some implementations, process 100 can use the motion data collected at block 102 and the contextual data received at block 104 as inputs to any suitable algorithm, calculation, or formula, to determine the likelihood. As a more particular example, in some implementations, process 100 can use any suitable machine learning algorithm or technique(s), as described below in more detail in connection with FIG. 2. In some implementations, a machine learning algorithm used by process 100 can be trained with any suitable training samples, as described below in more detail in connection with FIG. 2. In some implementations, process 100 can determine more than one likelihood, such as a likelihood that data collected from the sensor is of high enough quality to calculate different metrics. For example, in some implementations, process 100 can calculate a first likelihood that the sensor data will be of high enough quality to calculate a heart rate, and a second likelihood that the sensor data will be of high enough quality to calculate an HRV.

At 108, process 100 can determine whether the calculated likelihood exceeds a predetermined threshold (e.g., greater than 50%, greater than 70%, greater than 90%, and/or any other suitable threshold).

If, at 108, process 100 determines that the calculated likelihood does not exceed the predetermined threshold ("no" at 108), process 100 can proceed to block 112, described in more detail below. That is, process 100 can proceed to block 112 without making a measurement using the sensor. For example, process 100 can inhibit the processor of a wearable computing device and one or more sensors connected to the processor from being activated and from obtaining one or more sensor measurements.

If, at 108, process 100 determines that the calculated likelihood exceeds the predetermined threshold ("yes" at 108), process 100 can proceed to block 110. At 110, process 100 can make a measurement using the sensor. For example, in instances where the sensor is a PPG sensor, process 100 can transmit any suitable instructions that cause a light-emitting diode associated with the PPG sensor to produce light illuminating a patch of skin of a user of the user device and any suitable instructions that cause a photodiode associated with the PPG sensor to measure an amount of light transmitted and/or reflected by the skin of the user. In another example, process 100 can activate a processor associated with a user device from a sleep mode to an active mode. In some implementations, any suitable number of measurement samples can be received by process 100.

In some implementations, process 100 can calculate any suitable metrics using the recorded data. For example, in instances where the sensor is a PPG sensor and process 100 recorded measurements of an amount of light reflected and/or transmitted by the user's skin, process 100 can calculate metrics such as an instantaneous heart rate of the user, an average heart rate for the user based on any suitable time period (an average over the last second, an average over the last two seconds, and/or any other suitable time period), an HRV of the user, a respiration rate of the user, and/or any other suitable metric.

At 112, process 100 can collect information that indicates an accuracy of the likelihood calculation. In instances where the calculated likelihood exceeded the predetermined threshold at block 108 and where a sensor recording was made at block 110, process 100 can determine an accuracy of the data recorded by the sensor and/or an accuracy of the one or more metrics calculated based on the sensor data. For example, in instances where the sensor is a PPG sensor, process 100 can determine a confidence level corresponding to one or more metrics calculated based on the sensor data. As a more particular example, process 100 can determine a confidence level in a heart rate and/or an HRV calculated based on the sensor data. As another more particular example, process 100 can calculate a score indicating a quality of a metric calculated based on the sensor data, such as a score indicating a quality of a heart rate trace calculated based on the sensor data. As a specific example, process 100 can calculate a quality score based on a determination of an amount of noise in the heart rate trace, and/or based on any other suitable information.

In instances where the calculated likelihood did not exceed the predetermined threshold at block 108 and where block 110 was omitted, process 100 can collect any suitable information indicating the accuracy of the likelihood calculation. For example, in instances where the calculated likelihood indicated that a sensor reading would likely be of relatively poor quality because of a likelihood of excessive motion of the user device, process 100 can determine whether the prediction of excessive motion occurred based on any suitable information (e.g., information from a motion sensor, location information, and/or any other suitable information).

Process 100 can then return back to 102.

Note that, in some implementations, the information indicating the accuracy of the likelihood calculation can be used to update parameters used to determine the likelihood of high quality sensor readings for future predictions. For example, as described below in more detail in connection with block 206 of FIG. 2, the information can be used to create additional training samples for an algorithm used to determine the likelihood of high quality sensor readings.

Figure 2:
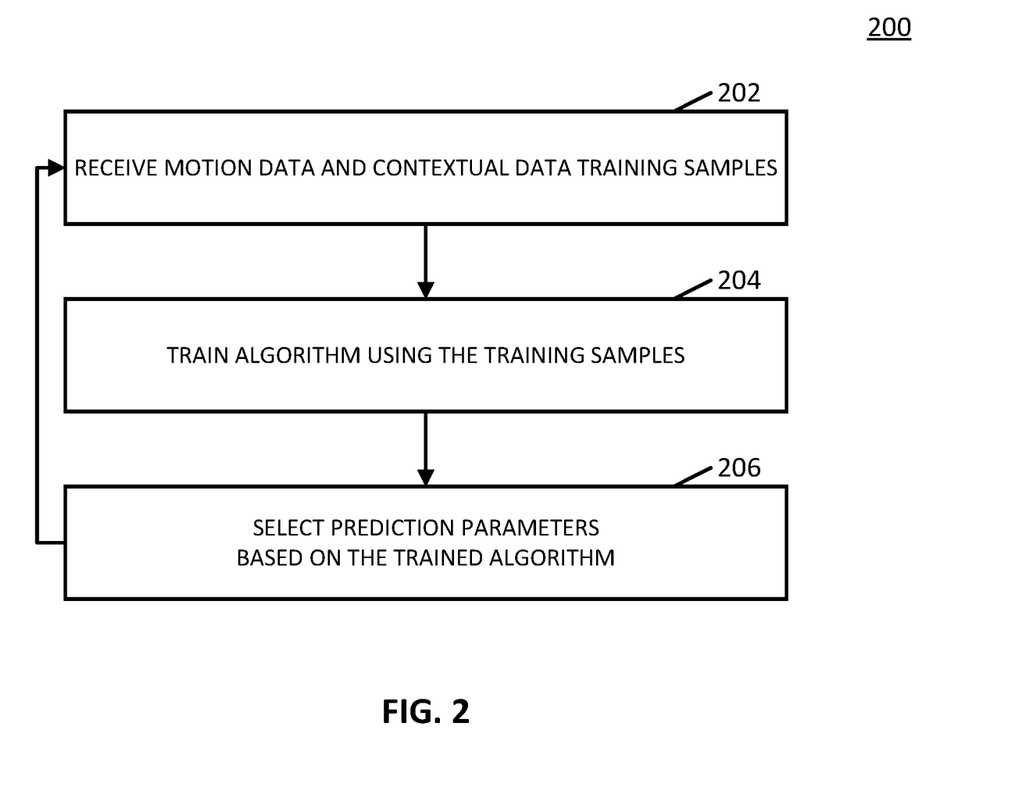
FIG. 2 shows an example of a process for determining parameters for predicting a likelihood that a sensor measurement will be of sufficient quality in accordance with some implementations of the disclosed subject matter.

Turning to FIG. 2, an example 200 of a process for determining parameters for determining a likelihood that a sensor reading will be of relatively high quality is shown in accordance with some implementations of the disclosed subject matter. In some implementations, blocks of process 200 can be implemented on any suitable device. For example, in some implementations, blocks of process 200 can be implemented on a user device associated with the sensor reading, such as a wearable computing device (e.g., a fitness tracker, a smartwatch, and/or any other suitable type of wearable computing device). As another example, in some implementations, blocks of process 200 can be implemented on a server, such as a server that receives data from one or more user devices and uses the received data to select parameters for an algorithm or function for determining the likelihood that a sensor reading will be of relatively high quality.

Process 200 can begin by receiving motion data and/or contextual data at 202. For example, in some implementations, the motion data can be recordings from a motion sensor (e.g., an accelerometer, a gyroscope, and/or any other suitable type of motion sensor) associated with a user device, as described above in connection with block 102 of FIG. 1. As another example, in some implementations, the contextual data can be information such as timing information (e.g., a current time of day, a current day of the week, and/or any other suitable timing information), environmental information (e.g., a current ambient light level, a current noise level, and/or any other suitable environmental information), a current activity of the user, and/or any other suitable contextual information, as described above in connection with block 104 of FIG. 1.

In some implementations, the received motion data and the received contextual data can be used as training samples by process 200. For example, in some implementations, the received motion data and/or the received contextual data can be paired with a score indicating a quality of a sensor reading. As a more particular example, in some implementations, motion data indicating motion of a user device (e.g., from an accelerometer associated with the user device) can be paired with an indication of a noise level of the sensor reading. In some such implementations, the noise level of the sensor reading can be on any suitable scale (e.g., a binary scale indicating whether the sensor reading was noisy or not, an average noise level, and/or any other suitable scale). In some implementations, the score indicating the quality of the sensor reading can be assigned manually and/or algorithmically. For example, a training sample can include the accelerometer samples paired with a 0, indicating that the PPG sensor readings from the corresponding time window were too noisy to be useful. As another specific example, a training sample can include the accelerometer samples paired with an average noise level of the PPG sensor readings from the corresponding time window.

In some implementations, each training sample can include motion data samples and sensor reading samples of any suitable duration. For example, in some implementations, a sliding window of a particular duration (e.g., five seconds, ten seconds, and/or any other suitable duration) can be used to create each training sample. As a more particular example, in an instance where the sensor reading corresponds to measurements from a PPG sensor associated with the user device, a training sample can include ten seconds of accelerometer data paired with an indication of a quality of the PPG sensor readings from the corresponding ten second window. In some implementations, a corresponding time window of sensor measurements can be a time window subsequent to the time window of the motion data measurements. Alternatively, in some implementations, a time window of the sensor measurements can overlap the time window of the motion data measurements with any suitable overlap duration.

Note that, in some implementations, the contextual information can be included in a training sample in any suitable manner. For example, in some implementations, a training sample can additionally include an indication of an amount of ambient light during a time window corresponding to the motion data and/or to the sensor readings. As another example, in some implementations, a training sample can include an indication of a time of day, an ambient temperature, a current activity of the user, and/or any other suitable contextual information during a time window corresponding to the motion data and/or to the sensor readings.

Note that, in instances where process 200 is performed by a server, process 200 can receive motion data, contextual data, and sensor readings from any suitable number of user devices (e.g., one, ten, fifty, one hundred, and/or any other suitable number) to construct training samples based on multiple user devices.

At 204, process 200 can train or construct an algorithm using the training samples received and/or constructed as described above in connection with block 202. In some implementations, process 200 can be any suitable type of algorithm. For example, in some implementations, process 200 can be a thresholding algorithm that determines a threshold of motion (as indicated by the motion data) for which the sensor reading is likely to be of high enough quality to calculate any suitable metrics. As a more particular example, in some implementations, process 200 can construct a histogram based on the motion data. As a specific example, a histogram can be generated of mean acceleration or mean jerk values over a time window of the motion data for each training sample. In some implementations, the data points used to construct the histogram can be tagged or labeled based on the score indicating a quality of the sensor reading for each training sample, as described above in connection with block 202.

As another example, in some implementations, process 200 can train a feature-based classifier using the training samples. In some implementations, the feature-based classifier can be any suitable type of classifier, such as a neural network, a random forest algorithm, a support vector machine, a logistic regression, and/or any other suitable type of classifier. In some implementations, process 200 can construct features using the motion data and/or the contextual data in any suitable manner. For example, in some implementations, for each training sample, process 200 can construct features using means and/or standard deviations of data samples corresponding to motion data for a particular training sample. As a more particular example, in some implementations, in instances where the motion data includes accelerometer readings over a ten second window, process 200 can construct features that include a mean acceleration over the ten second window, a standard deviation of the accelerometer measurements over the ten second window, and/or any other suitable features. In some implementations, each training sample can be associated with any suitable number of features. For example, in an instance where motion data associated with a training sample includes accelerometer data from a particular time window, process 200 can construct a group of features for the training sample that includes: a first mean corresponding to a mean acceleration for a first third of the particular time window, a first standard deviation corresponding to a standard deviation for the first third of the particular time window, a second mean corresponding to a mean acceleration for a second third of the particular time window, a second standard deviation corresponding to a standard deviation for the second third of the particular time window, a third mean corresponding to a mean acceleration for a last third of the particular time window, a third standard deviation corresponding to a standard deviation for a last third of the particular time window, and/or any other suitable features. Note that, in some implementations, process 200 can construct features based on the contextual data in any suitable manner. For example, in some implementations, process 200 can construct features that indicate timing information, ambient environmental information, and/or any other suitable features.

As yet another example, in some implementations, process 200 can train a convolutional neural network or a deep neural network model. In some such implementations, the neural network can use raw motion data as training samples. For example, in some implementations, a training sample can include raw accelerometer data from any suitable temporal window (e.g., ten seconds, and/or any other suitable duration of time). Additionally or alternatively, in some implementations, the neural network can use any other suitable data in training samples, such as data indicating a user's activities, data indicating ambient light, data indicating ambient temperature, a timing information, and/or any other suitable contextual information.

At 206, process 200 can select parameters for calculating a likelihood that a sensor reading is likely to be of relatively high quality and/or of high enough quality to calculate a particular metric. For example, in some implementations, in instances where the algorithm used (as described above in connection with block 204) is a thresholding algorithm, process 200 can select a threshold that, when applied to the motion data and/or contextual data, is likely to be associated with a sensor reading of acceptable quality. As a more particular example, process 200 can determine a threshold for a mean acceleration over a particular time period for which more than a predetermined percentage of sensor readings made in a subsequent time period (e.g., greater than 70%, greater than 90%, and/or any other suitable percentage) were of acceptable quality. As a specific example, process 200 can determine that more than 90% of sensor readings were of relatively high quality if the mean acceleration over a particular time window was less than a predetermined threshold. As another more particular example, process 200 can determine a threshold for a mean acceleration over a particular time period for which less than a predetermined percentage of sensor readings made in a subsequent time period (e.g., less than 20%, less than 10%, and/or any other suitable percentage) were of poor quality. As a specific example, process 200 can determine that more than 10% of sensor readings were of relatively poor quality if the mean acceleration over the particular time window exceeds a predetermined threshold. As another example, in instances where the algorithm used (as described above in connection with block 204) is a feature-based classifier and/or a neural network, process 200 can identify weights or other parameters converged on by the algorithm during training. As a more particular example, in some implementations, in instances where the algorithm used is a neural network, process 200 can identify weights for the neural network converged upon during an optimization of the weights, and/or identified in any other suitable manner.

In some implementations, the parameters identified by process 200 at block 206 can be used by process 100 to determine a likelihood that a sensor reading from a sensor associated with a user device (e.g., a PPG sensor, and/or any other suitable type of sensor) will record data of relatively high quality and/or of sufficient quality to calculate a particular metric (e.g., heart rate, HRV, and/or any other suitable metric) based on motion data and/or contextual data associated with the user device, as described above in connection with block 106 of FIG. 1. For example, in instances where the algorithm used is a thresholding algorithm and the parameters identified at block 206 include a threshold of acceleration for which more than a predetermined percentage of sensor readings were of relatively high quality, process 100 can determine whether a mean acceleration of acceleration data over a particular time window exceeds the threshold. As another example, in instances where the algorithm used is a neural network and the parameters identified at block 206 include weights for the neural network, process 100 can apply the weights to recorded motion data inputs and/or to contextual data to predict a likelihood that sensor readings for an subsequent time window will be of relatively high quality and/or of sufficient quality to calculate a particular metric.

Process 200 can, in some implementations, return to block 202 and receive additional motion data, contextual data, and sensor readings. Process 200 can then use the received data to construct additional training samples to update parameters for calculating the likelihood that a sensor reading will be usable.

Figure 3:
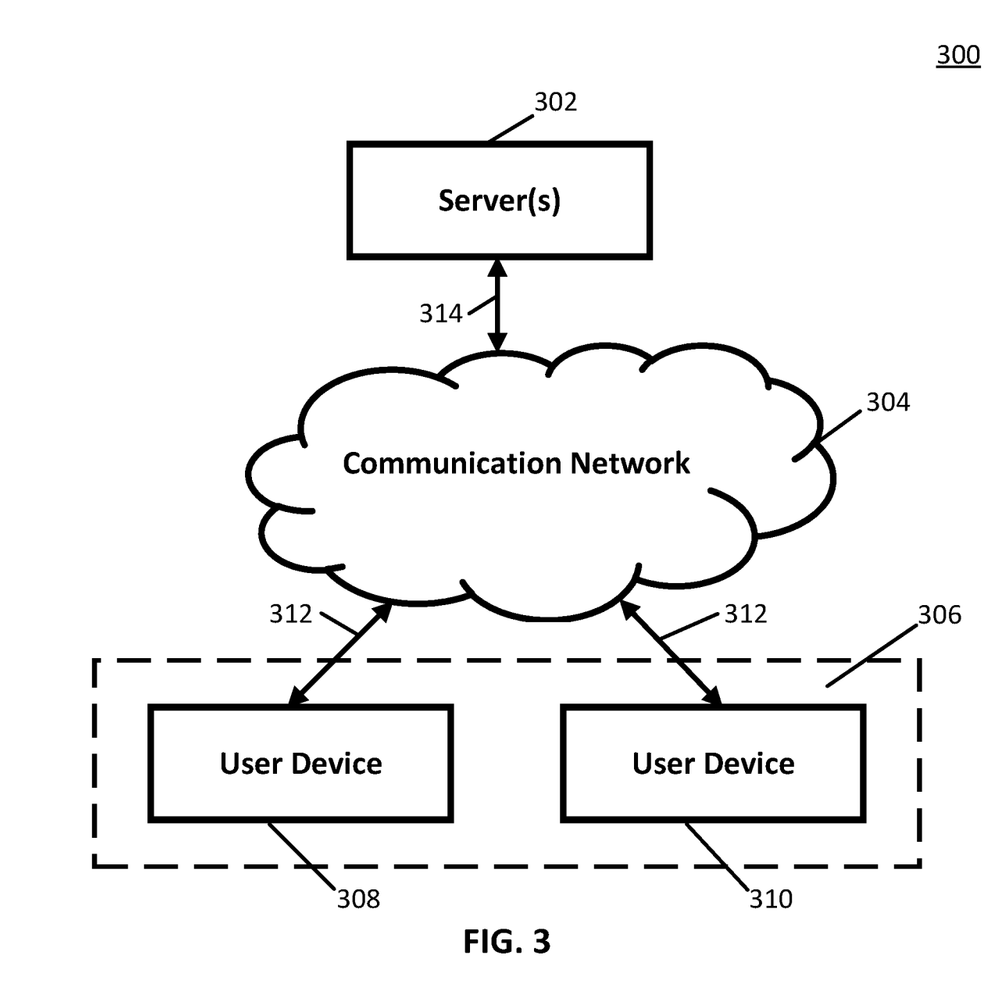
FIG. 3 shows a schematic diagram of an illustrative system suitable for implementation of mechanisms described herein for determining whether to make a sensor measurement in accordance with some implementations of the disclosed subject matter.

Turning to FIG. 3, an example 300 of hardware for determining whether to collect sensor measurements that can be used in accordance with some implementations of the disclosed subject matter is shown. As illustrated, hardware 300 can include a server 302, a communication network 304, and/or one or more user devices 306, such as user devices 308 and 310.

Server 302 can be any suitable server(s) for storing data and performing calculations. For example, in some implementations, server 302 can receive data from any suitable number of user devices that indicate motion of the user devices, contextual information associated with the user devices, and/or sensor readings from the user devices. In some implementations, server 302 can use the data to train any suitable algorithm for determining whether a sensor reading (e.g., from a PPG sensor, and/or any other suitable type of sensor) will produce data of high enough quality to perform a particular measurement, as described above in connection with FIG. 2. In some implementations, server 302 can be omitted.

Communication network 304 can be any suitable combination of one or more wired and/or wireless networks in some implementations. For example, communication network 304 can include any one or more of the Internet, an intranet, a wide-area network (WAN), a local-area network (LAN), a wireless network, a digital subscriber line (DSL) network, a frame relay network, an asynchronous transfer mode (ATM) network, a virtual private network (VPN), and/or any other suitable communication network. User devices 306 can be connected by one or more communications links (e.g., communications links 312) to communication network 304 that can be linked via one or more communications links (e.g., communications links 314) to server 302. The communications links can be any communications links suitable for communicating data among user devices 306 and server 302 such as network links, dial-up links, wireless links, hard-wired links, any other suitable communications links, or any suitable combination of such links.

User devices 306 can include any one or more user devices suitable for receiving motion data indication a motion of the user device, receiving readings from a sensor associated with the user device (e.g., a PPG sensor, and/or any other suitable type of sensor), determining whether a reading from the sensor is likely to yield relatively high quality data, and/or for performing any other suitable functions. For example, in some implementations, user devices 306 can include a wearable computing device, such as a fitness tracker, a smartwatch, and/or any other suitable type of user device. As another example, in some implementations, user devices 306 can include any other suitable type of user device, such as a mobile phone, a tablet computer, a laptop computer, a desktop computer, and/or any other suitable type of user device.

Although server 302 is illustrated as one device, the functions performed by server 302 can be performed using any suitable number of devices in some implementations. For example, in some implementations, multiple devices can be used to implement the functions performed by server 302.

Although two user devices 308 and 310 are shown in FIG. 3 to avoid over-complicating the figure, any suitable number of user devices, and/or any suitable types of user devices, can be used in some implementations.

Server 302 and user devices 306 can be implemented using any suitable hardware in some implementations. For example, in some implementations, devices 302 and 306 can be implemented using any suitable general purpose computer or special purpose computer. For example, a wearable computing device may be implemented using a special purpose computer. Any such general purpose computer or special purpose computer can include any suitable hardware.

Figure 4:
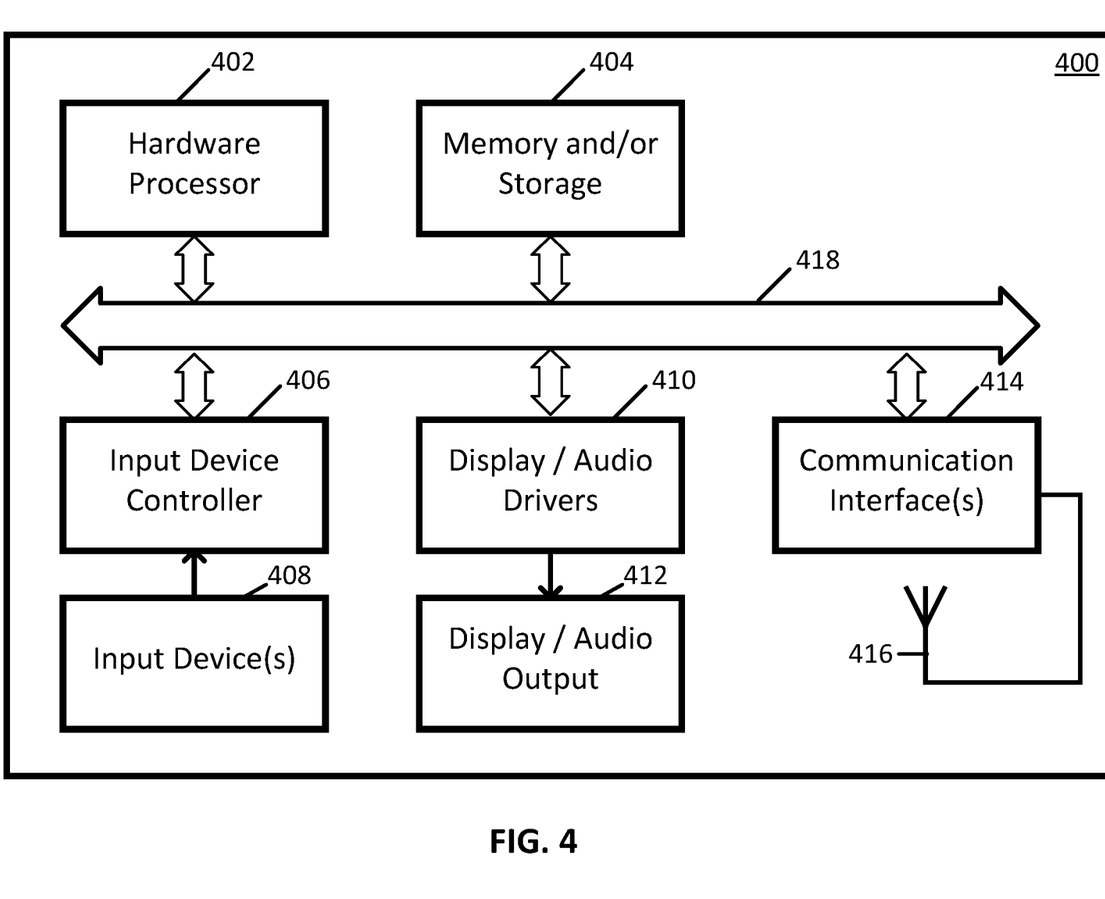
FIG. 4 shows a detailed example of hardware that can be used in a server and/or a user device of FIG. 3 in accordance with some implementations of the disclosed subject matter.

For example, as illustrated in example hardware 400 of FIG. 4, such hardware can include hardware processor 402, memory and/or storage 404, an input device controller 406, an input device 408, display/audio drivers 410, display and audio output circuitry 412, communication interface(s) 414, an antenna 416, and a bus 418.

Hardware processor 402 can include any suitable hardware processor, such as a microprocessor, a micro-controller, digital signal processor(s), dedicated logic, and/or any other suitable circuitry for controlling the functioning of a general purpose computer or a special purpose computer in some implementations. In some implementations, hardware processor 402 can be controlled by a server program stored in memory and/or storage 404 of a server, such as server 302 as shown in and described above in connection with FIG. 3. For example, the server program can cause hardware processor 402 to train an algorithm for determining a likelihood a sensor reading from a user device is likely to be of relatively high quality, as described above in connection with FIG. 2. In some implementations, hardware processor 402 can be controlled by a computer program stored in memory and/or storage 404 of a user device. For example, the computer program can cause hardware processor 402 to determine a likelihood that a measurement from a sensor will be of high quality as described above in connection with FIGS. 1 and 2, and/or perform any other suitable actions.

Memory and/or storage 404 can be any suitable memory and/or storage for storing programs, data, media content, and/or any other suitable information in some implementations. For example, memory and/or storage 404 can include random access memory, read-only memory, flash memory, hard disk storage, optical media, and/or any other suitable memory.

Input device controller 406 can be any suitable circuitry for controlling and receiving input from one or more input devices 408 in some implementations. For example, input device controller 406 can be circuitry for receiving input from a touchscreen, from a keyboard, from a mouse, from one or more buttons, from a voice recognition circuit, from a microphone, from a camera, from an optical sensor, from an accelerometer, from a gyroscope, from a temperature sensor, from a near field sensor, from a light sensor, and/or any other type of input device.

Display/audio drivers 410 can be any suitable circuitry for controlling and driving output to one or more display/audio output devices 412 in some implementations. For example, display/audio drivers 410 can be circuitry for driving a touchscreen, a flat-panel display, a cathode ray tube display, a projector, a speaker or speakers, and/or any other suitable display and/or presentation devices.

Communication interface(s) 414 can be any suitable circuitry for interfacing with one or more communication networks (e.g., communication network 304). For example, interface(s) 414 can include network interface card circuitry, wireless communication circuitry, and/or any other suitable type of communication network circuitry.

Antenna 416 can be any suitable one or more antennas for wirelessly communicating with a communication network (e.g., communication network 304) in some implementations. In some implementations, antenna 416 can be omitted.

Bus 418 can be any suitable mechanism for communicating between two or more components 402, 404, 406, 410, and 414 in some implementations.

Any other suitable components can be included in hardware 400 in accordance with some implementations.

In some implementations, at least some of the above described blocks of the processes of FIGS. 1 and 2 can be executed or performed in any order or sequence not limited to the order and sequence shown in and described in connection with the figures. Also, some of the above blocks of FIGS. 1 and 2 can be executed or performed substantially simultaneously where appropriate or in parallel to reduce latency and processing times. Additionally or alternatively, some of the above described blocks of the processes of FIGS. 1 and 2 can be omitted.

In some implementations, any suitable computer readable media can be used for storing instructions for performing the functions and/or processes herein. For example, in some implementations, computer readable media can be transitory or non-transitory. For example, non-transitory computer readable media can include media such as non-transitory forms of magnetic media (such as hard disks, floppy disks, and/or any other suitable magnetic media), non-transitory forms of optical media (such as compact discs, digital video discs, Blu-ray discs, and/or any other suitable optical media), non-transitory forms of semiconductor media (such as flash memory, electrically programmable read-only memory (EPROM), electrically erasable programmable read-only memory (EEPROM), and/or any other suitable semiconductor media), any suitable media that is not fleeting or devoid of any semblance of permanence during transmission, and/or any suitable tangible media. As another example, transitory computer readable media can include signals on networks, in wires, conductors, optical fibers, circuits, any suitable media that is fleeting and devoid of any semblance of permanence during transmission, and/or any suitable intangible media.

In situations in which the systems described herein collect personal information about users, or make use of personal information, the users may be provided with an opportunity to control whether programs or features collect user information (e.g., information about a user's social network, social actions or activities, profession, a user's preferences, or a user's current location). In addition, certain data may be treated in one or more ways before it is stored or used, so that personal information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

Accordingly, methods, systems, and media for predicting sensor measurement quality are provided.

Although the invention has been described and illustrated in the foregoing illustrative implementations, it is understood that the present disclosure has been made only by way of example, and that numerous changes in the details of implementation of the invention can be made without departing from the spirit and scope of the invention, which is limited only by the claims that follow. Features of the disclosed implementations can be combined and rearranged in various ways.

What is claimed is:

1. A method for predicting sensor measurement quality, the method comprising:
    measuring, using a wearable computing device that includes a processor and a sensor, information indicating motion of the wearable computing device during a first time period;
    determining contextual information associated with the wearable computing device;

determining a likelihood that one or more measurements from the sensor configured within the wearable computing device is of sufficient quality at a second time period for calculating a physiological metric using the one or more measurements from the sensor based the information indicating the motion of the wearable computing device during the first time period and the determined contextual information associated with the wearable computing device; and in response to determining that the likelihood exceeds a predetermined threshold, activating the processor and the sensor and collecting a measurement from the sensor at the second time period.

2. The method of claim 1, wherein the sensor is a photoplethysmography sensor and wherein the physiological metric is heart rate variability of a user of the wearable computing device.

3. The method of claim 1, further comprising identifying one or more parameters associated with the determination of the likelihood that the one or more measurements from the sensor configured within the wearable computing device is of sufficient quality for calculating the physiological metric using the one or more measurements from the sensor.

4. The method of claim 3, wherein the one or more parameters include a threshold associated with the information indicating the motion of the wearable computing device during the first time period, and wherein the likelihood is determined based on the threshold associated with information indicating the motion of the wearable computing device.

5. The method of claim 1, wherein the information indicating the motion of the wearable computing device includes an acceleration of the wearable computing device, and wherein the threshold associated with the information indicating the motion of the wearable computing device is a mean acceleration measured during the first time period.

6. The method of claim 1, wherein the parameters are determined based on a training set comprising a plurality of training samples, wherein a training sample from the plurality of training samples includes the information indicating the motion of the wearable computing device and a corresponding sensor measurement.

7. The method of claim 1, further comprising, in response to determining that the likelihood does not exceed the predetermined threshold, causing the identified one or more parameters to be updated and inhibiting the processor and the sensor of the wearable computing device from being activated.

8. The method of claim 1, further comprising updating the identified one or more parameters based on the motion of the wearable computing device during the first time period and based on the measurement from the sensor at the second time period.

9. A system for predicting sensor measurement quality, the system comprising:
a sensor; and
a hardware processor connected to the sensor, wherein the hardware processor is configured to:
measure information indicating motion of the wearable computing device during a first time period;
determine contextual information associated with the wearable computing device;
determine a likelihood that one or more measurements from the sensor configured within the wearable computing device is of sufficient quality at a second time period for calculating a physiological metric using the one or more measurements from the sensor based the information indicating the motion of the wearable computing device during the first time period and the determined contextual information associated with the wearable computing device; and in response to determining that the likelihood exceeds a predetermined threshold, activate the processor and the sensor and collecting a measurement from the sensor at the second time period.

10. The system of claim 9, wherein the sensor is a photoplethysmography sensor and wherein the physiological metric is heart rate variability of a user of the wearable computing device.

11. The system of claim 9, wherein the hardware processor is further configured to identify one or more parameters associated with the determination of the likelihood that the one or more measurements from the sensor configured within the wearable computing device is of sufficient quality for calculating the physiological metric using the one or more measurements from the sensor.

12. The system of claim 11, wherein the one or more parameters include a threshold associated with the information indicating the motion of the wearable computing device during the first time period, and wherein the likelihood is determined based on the threshold associated with information indicating the motion of the wearable computing device.

13. The system of claim 9, wherein the information indicating the motion of the wearable computing device includes an acceleration of the wearable computing device, and wherein the threshold associated with the information indicating the motion of the wearable computing device is a mean acceleration measured during the first time period.

14. The system of claim 9, wherein the parameters are determined based on a training set comprising a plurality of training samples, wherein a training sample from the plurality of training samples includes the information indicating the motion of the wearable computing device and a corresponding sensor measurement.

15. The system of claim 9, wherein the hardware processor is further configured to, in response to determining that the likelihood does not exceed the predetermined threshold, cause the identified one or more parameters to be updated and inhibiting the processor and the sensor of the wearable computing device from being activated.

16. The system of claim 9, wherein the hardware processor is further configured to update the identified one or more parameters based on the motion of the wearable computing device during the first time period and based on the measurement from the sensor at the second time period.

17. A non-transitory computer-readable medium containing computer executable instructions that, when executed by a processor, cause the processor to perform a method for predicting sensor measurement quality, the method comprising:
measuring, using a wearable computing device that includes a processor and a sensor, information indicating motion of the wearable computing device during a first time period;
determining contextual information associated with the wearable computing device;
determining a likelihood that one or more measurements from the sensor configured within the wearable computing device is of sufficient quality at a second time period for calculating a physiological metric using the one or more measurements from the sensor based the information indicating the motion of the wearable computing device during the first time period and the determined contextual information associated with the wearable computing device; and in response to determining that the likelihood exceeds a predetermined threshold, activating the processor and the sensor and collecting a measurement from the sensor at the second time period.

18. The non-transitory computer-readable medium of claim 17, wherein the method further comprises identifying one or more parameters associated with the determination of the likelihood that the one or more measurements from the sensor configured within the wearable computing device is of sufficient quality for calculating the physiological metric using the one or more measurements from the sensor.

19. The non-transitory computer-readable medium of claim 17, wherein the method further comprises, in response to determining that the likelihood does not exceed the predetermined threshold, causing the identified one or more parameters to be updated and inhibiting the processor and the sensor of the wearable computing device from being activated.

20. The non-transitory computer-readable medium of claim 17, wherein the method further comprises updating the identified one or more parameters based on the motion of the wearable computing device during the first time period and based on the measurement from the sensor at the second time period.

* * * * *